United States Patent [19]

Osborn

[11] Patent Number: 5,009,595
[45] Date of Patent: Apr. 23, 1991

[54] DENTAL MOUTH PROP

[76] Inventor: Carl F. Osborn, 106 Stuyvesant Rd., Asheville, N.C. 28803

[21] Appl. No.: 386,157

[22] Filed: Jul. 28, 1989

[51] Int. Cl.⁵ .............................................. A61C 5/00
[52] U.S. Cl. ................................................ 433/140
[58] Field of Search .......................... 433/140, 136, 93

[56] References Cited

U.S. PATENT DOCUMENTS

| | | | |
|---|---|---|---|
| 667,441 | 2/1901 | Hare | 433/93 |
| 692,281 | 2/1902 | Hare | 433/93 |
| 1,498,219 | 6/1924 | Williams | 433/140 |
| 2,823,455 | 2/1958 | Sprague | 433/140 |
| 3,483,619 | 12/1969 | Smith | 433/140 |
| 3,722,101 | 3/1973 | Via, Jr. | 433/140 |
| 3,924,333 | 12/1975 | Erickson | 433/93 |
| 4,179,815 | 12/1979 | Hoffman | 433/140 |

FOREIGN PATENT DOCUMENTS 2452279 11/1980 France .............................. 433/140

Primary Examiner—John J. Wilson
Assistant Examiner—Michael Lynch
Attorney, Agent, or Firm—David M. Carter

[57] ABSTRACT

There is provided an improved mouth prop for dental patients in the form of a tapered block made of pliable styrene material. A portion of one side of the block is concaved so as to more readily provide access to the patient's mouth and improve visibility. The block includes a pair of flanges extending from the top and bottom thereof on the cheek side to aid in stabilizing the block and to keep soft tissue away from the working area of the mouth and to channel saliva away from the working area.

10 Claims, 1 Drawing Sheet

DENTAL MOUTH PROP

BACKGROUND OF THE INVENTION

This invention relates to dentistry apparatus. More particularly it relates to mouth props for dental patients.

Dental mouth props are devices which are inserted into the patient's mouth between upper and lower teeth to keep the mouth opened in a fixed position while the dentist is working in the patient's mouth. Normally the teeth on one side of the mouth contacts the mouth prop while the dentist is working on teeth on the opposite side. Mouth props are desirable, particularly in order to enhance the efficiency of the dentist so the dentist does not have to continually remind the patient to keep the mouth open at a certain angle and also so that the dentist does not have to be concerned with the patient inadvertently biting his or her hands. Props also act as comfortable rests for patient.

Many different designs of mouth props have been used and/or have been disclosed in the literature, however those mouth props are inconvenient to use and are uncomfortable.

Examples of prior art mouth props are shown in U.S. Pat. Nos. 3,722,101 issued to Via, 3,483,619 issued to Smith, 692,281 issued to Hare, DES 267,586 issued to Halten, 4,179,815 issued to Hoffman, 2,570,459 issued to Kreider, DES 212,992 issued to Scaler, and 3,090,122 issued to Erickson. The Via patent discloses a polygonal shaped mouth prop which may be made of a foam material such as polyeurethane so that when the teeth indent into the material the block is supposed to lock in place. Furthermore, the Via prop may be tapered having a long front end and a short back end to better fit the teeth. However the Via prop suffers from several drawbacks. The Via prop takes up quite a bit of space in the mouth thus competing with space where the dentist works. Also the Via prop is somewhat unstable.

OBJECTS OF THE INVENTION

It is therefore one object of this invention to provide an improved dental mouth prop.

It is another object to provide a mouth prop which is inexpensive to produce, easy to use and is comfortable to the patient.

It is another object to provide a mouth prop which is disposable to aid in infection control.

It is still another object to provide a dental mouth prop which provides for substantial room in the mouth for the dentist to work and it is stable.

SUMMARY OF THE INVENTION

In accordance with one form of this invention there is provided a mouth prop for dental patients which includes a block of substantially unitary construction. The block is somewhat tapered and thus has a long end and a short end. The block has top and bottom sloped surfaces for providing resting areas for the teeth. A portion of the block is thinner than other portions, thereby enhancing access to the patient's mouth. Preferably the front portion beginning at the long end of the block is concaved forming the thinness of the front portion. Also, preferably the block is constructed of a pliable nonelastic material such as polystyrene so that the patient may bite into the block to provide comfort and some stability. Also in the preferred embodiment stability is enhanced by a pair of flanges extending above the top surface and below the bottom surface of the block. Preferably these flanges extend only on the cheek or facial side of the prop, thus there are no lingual flanges as are on many mouth props, thereby allowing better vision and accuracy on the lingual teeth on the side prop is placed.

BRIEF DESCRIPTION OF THE DRAWINGS

The subject matter which is regarded as the invention is set forth in the appended claims. The invention itself, however, together with further objects and advantages thereof, may be better understood by reference to the following description taken in conjunction with the accompanying drawings in which:

DESCRIPTION OF THE PREFERRED EMBODIMENT

Figure 1:
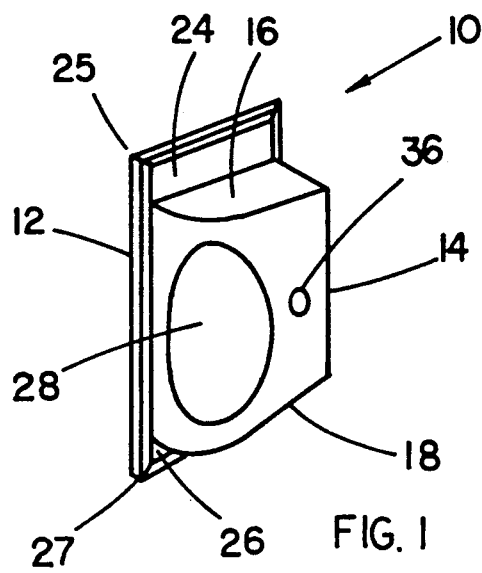
FIG. 1 is a pictorial view of a block showing one form of the invention.

Referring now more particularly to FIGS. 1 through 7, there is provided mouth prop or block 10 which is preferably constructed from a single piece of a pliable yet nonelastic material such as, for example, non-halogenated expanded polystyrene. Such a foamed material is lightweight and permits the patient to bite into the prop without destroying the prop, to provide comfort to the patient and to somewhat stabilize the prop in the mouth.

Mouth prop 10 includes a long end 12 and a short end 14 thereby resulting in a prop which is wedge shaped. The wedge shape conforms to the shape formed by the surfaces of the upper and lower teeth when the mouth is open. The mouth prop includes upper sloping surface 16 and lower sloping surface 18. Upper and lower surfaces 16 and 18 respectively receive upper teeth 20 and lower teeth 22. Flange 24 extends above upper surface 16 and flange 26 extends below lower surface 18 both on the cheek side. The flanges follow the sloping contour of upper and lower surfaces 16 and 18.

Preferably the flanges are made of the same material as the remainder of the block. Thus the prop, including its flanges, may be formed from a single unitary piece of polystyrene. Alternatively, the flanges could be formed by gluing a stiff sheet of material to the cheek side of the mouth prop.

Figure 2:
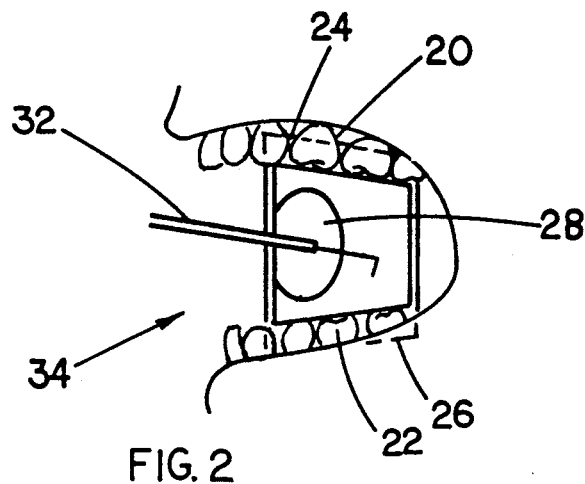
FIG. 2 is another pictorial view of the block of FIG. 1 showing the block inside a patient's mouth with a dental tool being used in the mouth.
Figure 3:
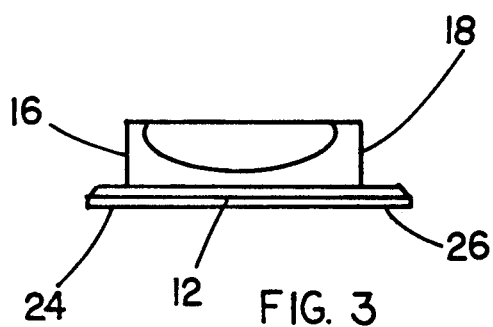
FIG. 3 is a front elevational view of the mouth prop of FIG. 1.
Figure 4:
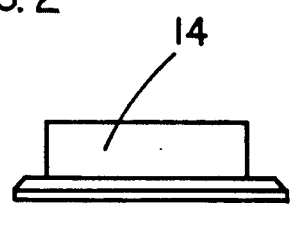
FIG. 4 is a rear elevational view of the mouth prop of FIG. 1.
Figure 5:
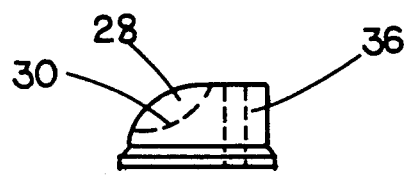
FIG. 5 is a side elevational view of the mouth prop of FIG. 1.
Figure 6:
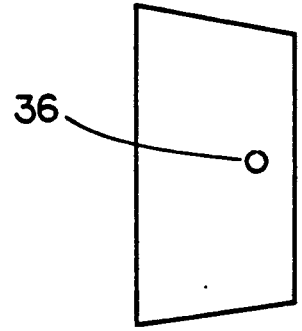
FIG. 6 is a bottom plan view of the mouth prop of FIG. 1.

As can be seen from FIG. 2, flanges 24 and 26 extend beyond the chewing surfaces of teeth 20 and 22 on the cheek side of the teeth thereby adding stability to the mouth prop while it is in the patient's mouth. Furthermore, flanges 24 and 26 keep soft tissue away from the dentist's working area and help channel saliva away from the working area. Flanges 24 and 26 include tips 25 and 27 which gently press into the buccal mucosa to aid in stabilizing the prop.

The mouth prop includes concaved portion 28 which causes a major portion of long end 12 to be thinner than short end 14. Concavity is accomplished by molding the polystyrene forming a contour shown by dotted line 30 in FIG. 4. As can be seen in FIG. 2, this concaved portion 28 provides room for the dentist or assistant to have additional working area and to more readily place instruments such as drill 32 or a vacuum into the mouth of the patient, which is generally indicated as 34. Also visibility into the mouth is expanded. Furthermore, the flanges 24 and 26 are on the cheek side providing access to the lingual and palatial surfaces of the teeth which grip the prop. Thus the mouth prop will not tend to interfere with the work of the dentist as prior mouth props have done. Hole 36 preferably is formed through a portion of the block so as to permit the practitioner to place dental floss or a cord therethrough as a safety feature in the event that the patient swallows the mouth prop.

Figure 7:
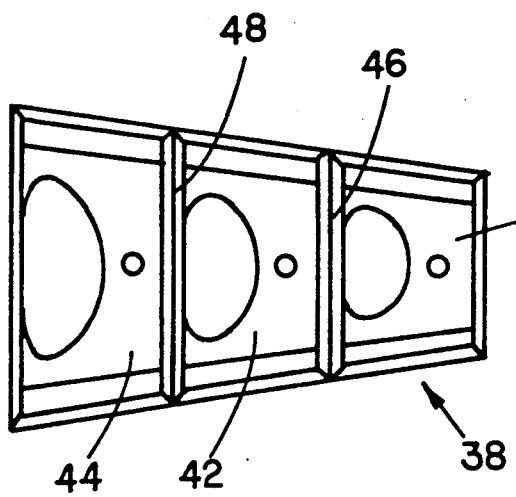
FIG. 7 is a top plan view of a group of mouth props of FIG. 1 with different sizes being attached together.

Referring now to FIG. 7, there is shown unitary structure 38 which is formed from a mold used to produce a plurality of different sized mouth blocks 40, 42, and 44. As can be seen, the plurality of mouth blocks are arranged in a row and all are attached to one another. There is a weakened section 46 between blocks 40 and 42 and a weakened section 48 between blocks 42 and 44 so that each block may be readily removed from the row of blocks by hand.

Thus a new mouth block is provided which is easy to manufacture and which is made of a one piece molded material. It is stable in the mouth in that flanges are used which rest against the sides of the teeth on the cheek or facial side. The facial musculature presses against flange side of the mouth prop and aids in retention. Furthermore since the preferred material is a soft pliable but nonelastic material the teeth penetrate a portion thereof, thereby enhancing stability. Also, the block does not interfere with the normal workings of the dentist because of its concaved design.

From the foregoing description of the preferred embodiment of the invention, it will be apparent that many modifications may be made therein. It will be understood however that this embodiment of the invention is intended as an exemplification of the invention only and that the invention is not limited thereto. It is to be understood therefore that it is intended in the appended claims however all such modifications will fall within the true spirit and scope of the invention.

I claim:

1. A mouth prop for dental patients comprising:
   a block; said block being of a substantially unitary construction; said block being somewhat tapered in shape wherein said block has a long end and a short end; said block having a substantially straight and continuous top sloping surface and a substantially straight continuous bottom sloping surface for providing resting areas for certain teeth; a portion of said block near said long end being thinner than other portions of said block, thereby enhancing access to the patient's mouth.

2. A mouth prop as set forth in claim 1 wherein a portion of one side of said block is concaved near said long end.

3. A mouth prop as set forth in claim 2 further including flanges extending above the top surface and below said bottom surface of said block on the side of the block opposite to the concaved side.

4. A mouth prop as set forth in claim 3 wherein said flanges are respectively tapered in the same direction as said top and bottom surfaces.

5. A mouth prop as set forth in claim 1 wherein said block is constructed of a pliable nonelastic material.

6. A mouth prop as set forth in claim 5 wherein said material is expanded polystyrene.

7. A mouth prop as set forth in claim 1 further including a hole at least part way through said block.

8. A mouth prop as set forth in claim 1 further including a plurality of said blocks removably attached to one another.

9. A mouth prop as set forth in claim 8 wherein each block is of a different size; said blocks are attached in a row arranged in descending order of size.

10. A mouth prop as set forth in claim 8 further including a weakened section between each of said blocks.

* * * * *